United States Patent [19]
Regnier et al.

[11] 4,260,610
[45] Apr. 7, 1981

[54] DISUBSTITUTED PIPERAZINES

[75] Inventors: Gilbert Regnier, Chatenay-Malabry; Roger Canevari, Elancourt; Michel Laubie, Vaucresson; Jean-Claude Poignant, Bures, all of France

[73] Assignee: Science Union Et Cie, Suresnes, France

[21] Appl. No.: 957,659

[22] Filed: Nov. 3, 1978

[30] Foreign Application Priority Data

Nov. 9, 1977 [GB] United Kingdom .............. 46646/77

[51] Int. Cl.³ .................. A61K 31/495; C07D 411/14; C07D 417/14
[52] U.S. Cl. .................................... 424/250; 424/251; 544/295; 544/368
[58] Field of Search ...................... 544/295, 369, 368; 424/250, 251

[56] References Cited

U.S. PATENT DOCUMENTS

| | | | |
|---|---|---|---|
| 3,299,067 | 1/1967 | Regnier et al. | 544/295 |
| 3,489,757 | 1/1970 | Koppe et al. | 544/369 |
| 3,585,193 | 6/1971 | Regnier et al. | 544/295 |
| 3,944,551 | 3/1976 | Regnier et al. | 544/369 |
| 3,954,765 | 5/1976 | Regnier et al. | 544/369 |

*Primary Examiner*—Paul M. Coughlan, Jr.
*Attorney, Agent, or Firm*—Gordon W. Hueschen

[57] ABSTRACT

Disubstituted piperazines of the formula:

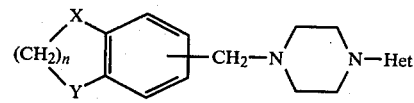

in which:
n is 1 or 2,
X is oxygen and Y is sulfur or sulfonyl or X and Y are both sulfur or sulfonyl, and
Het is a 5- or 6-membered heterocyclic radical having from 1 to 3 hetero atoms inclusive selected from nitrogen and sulfur and optionally substituted by one or more alkyl each having from 1 to 5 carbon atoms inclusive.

These compounds may be used as medicines, especially in the treatment of central nervous system disorders and Parkinson's disease.

5 Claims, No Drawings

DISUBSTITUTED PIPERAZINES

The present invention provides disubstituted piperazines of the formula:

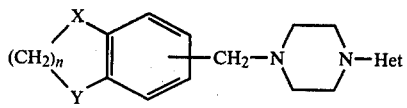
I in which:
- n is selected from 1 and 2;
- X is an oxygen atom and
- Y is selected from the group consisting of a sulfur atom and a sulfonyl radical, or
- X and Y have the same meaning selected from sulfur atoms and sulfonyl radicals, and
- Het is selected from the group consisting of unsubstituted, mono- and poly-substituted 5- and 6-membered heterocyclic radicals each having from 1 to 3 hetero-atoms inclusive selected from the group consisting of nitrogen and sulfur atoms; the substituents, if any, being selected from alkyl radicals having from 1 to 5 carbon atoms inclusive. As such heterocyclic radicals, there may be mentioned for example, pyridyl, pyrimidinyl, thiazolyl and thiadiazolyl radicals.

Furthermore, the compounds of the formula I wherein n is 1, X is an oxygen atom, Y is selected from the group consisting of a sulfur atom and a sulfonyl radical and Het is selected from the group consisting of pyridyl, pyrimidinyl, thiazolyl and thiadiazolyl radicals, are particularly interesting.

The present invention also provides acid addition salts, especially physiologically tolerable acid addition salts, of compounds of the formula I.

The present invention also provides a process for preparing compounds of the formula I which comprises condensing a halo compound of the formula

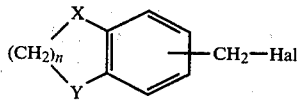
II in which n, X and Y have the meanings given above, and Hal is a chlorine or a bromine atom, with a N-monosubstituted piperazine of the formula

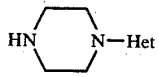
III in which Het has the meaning given above; or condensing a halo compound of the formula

IV in which Het and Hal have the meanings given above, with a N-monosubstituted piperazine of the formula

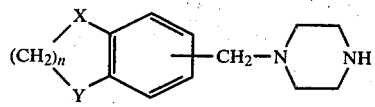
V in which n, X and Y have the meanings given above.

The above processes are advantageously carried out in solution in an aromatic compound, an aliphatic amide, for example, dimethylformamide, or an alcohol having a high boiling point, for example butanol or pentanol. It is advantageous to carry out the processes at a temperature of from 110° to 140° C., in the presence of an acceptor for the hydrogen halide formed during the course of the reaction. As such acid acceptors, there may be mentioned, for example alkali metal salts of carbonic acid, for example sodium or potassium carbonate, and organic bases, for example triethylamine. If desired, there may be used an excess of the monosubstituted piperazine of the formula III or V, the excess acting as the acid acceptor.

The present invention also provides a process for preparing compounds of the formula I which comprises submitting a mixture of an aldehyde of the formula

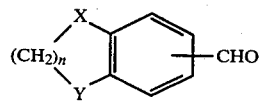
VI in which n, X and Y have the meanings given above, and a N-monosubstituted piperazine of the formula III given above, to an alkylating reduction using hydrogen at a pressure of from 5 to 7 atmospheres in the presence of palladium-on-charcoal in a slightly polar aprotic solvent, for example ethyl acetate.

Such a process is advantageously carried out by submitting to hydrogenation under a hydrogen pressure of from 5 to 7 atmospheres, a substantially equimolar mixture of the compounds of the formulae III and VI, in solution in ethyl acetate, in the presence of such a quantity of palladium-on-charcoal such that the weight of palladium is from 0.15 to 0.2% of the total weight of the reactants of the formulae III and VI, at a temperature of from 50° to 80° C.

The starting materials used for these processes are known compounds, or they may be prepared according to methods described in the literature for preparing similar compounds, as mentioned in the following Examples.

The compounds of the formula I are weak bases which may be converted by treatment with acids into acid addition salts. As acids which may be used for the formation of these addition salts, there may be mentioned for example, in the mineral series; hydrochloric, hydrobromic, sulfuric and phosphoric acids; and in the organic series: acetic, propionic, maleic, fumaric, tartaric, citric, oxalic, benzoic, methanesulfonic and isethionic acids.

The compounds of the formula I may be purified by physical methods, for example by distillation, crystallization or chromatography, or by chemical methods, for example by formation of an addition salt followed by crystallization of the latter and decomposition thereof with an alkaline agent.

The compounds of the formula I and physiologically tolerable acid addition salts thereof possess valuable pharmacological and therapeutic properties, especially dopaminergic agonistic and anti-Parkinson properties, and furthermore anti-inflammatory, anti-hypertensive and peripheral vasodilating properties. They may therefore be used as medicines, especially in the treatment of central nervous system disorders, and Parkinson's disease.

Their toxicity is low and their $LD_{50}$ determined in mice is higher than 200 mg/kg P.O. and higher that 100 mg/kg I.P.

Their neurologic properties were evidenced in the rats and mice by modifications observed on the stereotypy, motility and excitation.

In mice, the average effective dose is from 25 to 50 mg/kg by intraperitoneal route. At this dose, there were observed a decrease of motility and tonus.

The scores of C N S stimulation or stereotypy were determined according to the method of Quinton and Halliwell, Nature 200 No. 4902 p. 178 (1963). According to the tested compounds, there were observed, for 3 hours, scores of up to 238 with a dose of 80 mg/kg I.P., and up to 227 with a dose of 80 mg/kg P.O.

The present invention therefore also provides pharmaceutical compositions comprising as active ingredient a compound of the formula I or a physiologically tolerable acid addition salt thereof, in admixture or conjunction with a pharmaceutically suitable carrier, such for example as distilled water, glucose, lactose, starch, talc, magnesium stearate, ethyl cellulose or cocoa butter.

The so-obtained pharmaceutical compositions are advantageously in unit dosage form and may contain from 25 to 250 mg of the active ingredient.

These pharmaceutical compositions may be in form of tablets, dragees, capsules, suppositories or injectable or drinkable solutions and may be administered by oral, rectal or parenteral route at a dose of 25 to 250 mg, 2 to 6 times a day.

The following examples illustrate the invention, the melting points being determined in a capillary tube unless otherwise stated.

EXAMPLE 1

1-[(2H)-1,3-benzoxathiol-5-yl methyl]-4-(thiazol-2-yl)piperazine

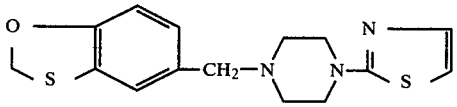

A solution of 13.6 g of 1-(thiazol-2-yl)piperazine and 8.5 g of 5-chloromethyl-(2H)-1,3-benzoxathiole in 150 ml of xylene and 3 ml of dimethyl formamide was refluxed for 3 hours. Then, the mixture was cooled and the so-formed 1-(thiazol-2-yl)piperazine hydrochloride was filtered off. The xylene filtrate was extracted several times with a 2 N solution of methane sulfonic acid. The acid juices were decanted off then rendered alkaline with an excess of potassium carbonate. The solution was extracted several times with chloroform. The chloroform solution was washed with water then dried over potassium carbonate, and the solvent was evaporated off. There were obtained 14 g of a semi-crystalline residue, which recrystallized in 30 ml of ethanol gave 9.8 g of beige crystals of 1-[(2H)-1,3-benzoxathiol-5-yl methyl]-4-(thiazol-2-yl)piperazine melting at 80°–81° C.

The starting 5-chloromethyl-(2H)-1,3-benzoxathiole, in the form of raw oil, was obtained by chlorination by the means of SO $Cl_2$ in ether, of 5-hydroxymethyl-(2H)-1,3-benzoxathiole (B.P./0.2 mmHg: 145°–150° C., $n_D{}^{22} = 1.627$), itself prepared by reducing with Al Li $H_4$ in ether the corresponding 5-formyl-(2H)-1,3-benzoxathiole, M.P. (Kofler)=76° C., itself prepared by treating, with dichloromethyl butyl ether and Ti $Cl_4$ in methylene chloride, (2H)-1,3-benzoxathiole prepared according to S. CABBIDU et al., Synthesis 1977 (12) 797.

EXAMPLES 2 to 5

The following compounds were prepared according to the process described in Example 1:

(2) 1-[3,3-dioxo-(2H)-1,3-benzoxathiol-6-yl methyl]-4-(thiazol-2-yl)piperazine, M.P. 164°–165° C., starting from 1-(thiazol-2-yl)piperazine and 6-bromomethyl-3,3-dioxo-(2H)-1,3-benzoxathiole, M.P. 146° C., itself prepared by bromination, by the means of N-bromo succinimide in carbon tetrachloride, of 6-methyl-3,3-dioxo-(2H)-1,3-benzoxathiole, M.P. 148° C., itself prepared by oxydation with $H_2O_2$ in $CH_3COOH$ of 6-methyl-(2H)-1,3-benzoxathiole prepared according to CABBIDU et al. Synthesis 1977 (12) 797.

(3) 1-[3,3-dioxo-(2H)-1,3-benzoxathiol-5-yl methyl]-4-(thiazol-2yl)piperazine, M.P. 193°–195° C., starting from 1-(thiazol-2-yl)piperazine and 5-bromomethyl-3,3-dioxo-(2H)-1,3-benzoxathiole, M.P. 190C, itself prepared by bromination by the means of N-bromosuccinimide in carbon tetrachloride of 5-methyl-3,3-dioxo-(2H)-1,3-benzoxathiole, M.P. 128° C., itself prepared by oxydation with $H_2O_2$ in $CH_3COOH$ of 5-methyl-(2H)-1,3-benzoxathiole prepared according to CABBIDU et al., Synthesis 1977 (12) 797.

(4) 1-[(2H)-1,3-benzoxathiol-5-yl methyl]-4-(2-pyridyl)piperazine, M.P. 102°–103° C., starting from 1-(2-pyridyl)piperazine and 5-chloromethyl-(2H)-1,3-benzoxathiole.

(5) 1-[(2H)-1,3-benzodithiol-5-yl methyl]-4-(2-pyridyl)piperazine, starting from 1-(2-pyridyl)piperazine and 5-bromomethyl-(2H)-1,3-benzodithiole.

EXAMPLE 6

1-[(2H)-1,3-benzoxathiol-5-yl methyl]-4-(1,3,4-thiadiazol-2-yl)piperazine

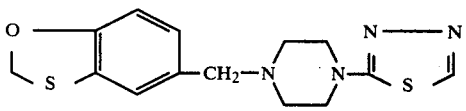

A solution of 4 g of 2-bromo-1,3,4 thiadiazole and 13 g of 1-[(2H)-1,3-benzoxathiol-5-yl methyl]piperazine in 200 ml of xylene and 10 ml of anhydrous dimethylformamide was refluxed for 3 hours. Then, the mixture was cooled, the crystals of 1-[(2H)-1,3-benzoxathiol-5-yl methyl]piperazine hydrobromide formed during the reaction were suctioned off, and the xylene filtrate was extracted several times with a 2 N solution of methane sulfonic acid. The acid layer was decanted off then rendered alkaline with an excess of potassium carbonate, and the raw base extracted with chloroform. The organic solution was washed with water, dried over dry potassium carbonate, and the solvent was evaporated off. There were obtained 8 g of an oily residue which was submitted to a high pressure liquid chromatography (Waters apparatus) in the system CH$_2$Cl$_2$-methanol; 98-2.

After evaporation of the different fractions, there were obtained 1.6 g of 1-[(2H)-1,3-benzoxathiol-5-yl methyl]-4-(1,3,4-thiadiazol-2-yl)piperazine, dihydrochloride, M.P. 258°–262° C.

The starting 1-[(2H)-1,3-benzoxathiol-5-yl methyl]-piperazine, M.P. of its dihydrochloride: 275°–278° C., was prepared by hydrolysis with alcoholic potassium hydroxyde of the corresponding formyl derivative, raw oil itself prepared by condensing 5-chloromethyl-(2H)-1,3-benzoxathiole with an excess of 1-formyl piperazine.

The starting 2-bromo-1,3-4-thiadiazole was prepared according to the method of GOERDELER et als, Ber. 84, 1534 (1956).

EXAMPLES 7 to 10

The following compounds were prepared according to the process described in Example 6.

(7) 1-(3,3-dioxo-(2H)-1,3-benzoxathiol-6-yl methyl)-4-(1,3,4-thiadiazol-2-yl)piperazine, starting from 2-bromo-1,3,4-thiadiazole and 1-[3,3-dioxo-(2H)-1,3-benzoxathiol-6-yl methyl]piperazine, dihydrochloride, M.P. 262°–265° C., itself prepared by hydrolysis with alcoholic potassium hydroxyde of the corresponding formyl derivative.

(8) 1-[(2H)-1,3-benzodithiol-5-yl methyl]-4-(1,3,4-thiadiazol-2-yl)piperazine, starting from 2-bromo-1,3,4-thiadiazole and 1-[(2H)-1,3-benzodithiol-5-yl methyl]-piperazine.

(9) 1-(1,4-benzoxathian-6-yl methyl)-4-(1,3,4-thiadiazol-2-yl)piperazine, starting from 2-bromo-1,3,4-thiadiazole and 1-(1,4-benzoxathian-6-yl methyl)piperazine.

(10) 1-(1,4-benzodithian-6-yl methyl)-4-(1,3,4-thiadiazol-2-yl)piperazine, starting from 2-bromo-1,3,4-thiadiazole and 1-(1,4-benzodithian-6-yl methyl)piperazine.

EXAMPLE 11

1-[(2H)-1,3-benzoxathiol-5-yl methyl]-4-(pyrimidin-2-yl)piperazine

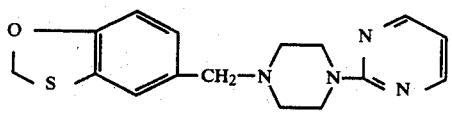

A solution of 16.6 g of 5-formyl-(2H)-1,3-benzoxathiole and 18.6 g of 1-(pyrimidin-2-yl)piperazine in 150 ml of ethyl acetate was hydrogenized under a pressure of hydrogen within the range of from 5 to 7 atmospheres, in the presence of 2 to 5 g of palladised charcoal containing 10% of palladium, at a temperature of 50° C. After the absorption of the theoretical amount of hydrogen, the catalyst was filtered off and the solvent was evaporated under reduced pressure. Th crystalline residue was recrystallized from 60 ml of ethanol and there were obtained 21 g of beige crystals of 1-[(2H)-1,3-benzoxathiol-5-yl methyl]-4-(pyrimidin-2-yl)piperazine, melting at 90°–91° C.; M.P. of its dihydrochloride: 270° C. with decomposition.

The following examples illustrate the pharmaceutical compositions containing as active ingredient a compound of the general formula I:

EXAMPLE 12

Formulation for one I.V. injectable ampul containing, as active ingredient, 25 mg of 1-[(2H)-1,3-benzoxathiol-5-yl methyl]-4-(1,3,4-thiodiazol-2-yl)piperazine

| | |
|---|---|
| 1-[(2H)-1,3-benzoxathiol-5-yl methyl]-4-(1,3,4-thiadiazol-2-yl) piperazine dihydrochloride | 0.0308g |
| sodium chloride | 0.04g |
| distilled water for I.V. injectable preparation q.s.p. | 5ml |

EXAMPLE 13

Formulation for one capsule containing, as active ingredient, 100 mg of 1-[(2H)-1,3-benzoxathiol-5-yl methyl]-4-(pyrimidin-2-yl)piperazine

| | |
|---|---|
| 1-[(2H)-1,3-benzoxathiol-5-yl methyl]-4-(pyrimidin-2-yl) piperazine dihydrochloride | 0.125g |
| microcristalline cellulose | 0.075g |
| colloidal silica | 0.0005g |
| polyvinylpyrrolidone | 0.005g |
| capsule No. 1 | 1 |

We claim:

1. A compound which is 1-[(2H)-1,3-benzoxathiol-5-yl methyl]-4-(thiazol-2-yl)piperazine or a physiologically tolerable acid addition salt thereof.

2. A compound which is 1-[(2H)-1,3-benzoxathiol-5-yl methyl]-4-(1,3,4-thiadiazol-2-yl)piperazine or a physiologically tolerable acid addition salt thereof.

3. A compound which is 1-[(2H)-1,3-benzoxathiol-5-yl methyl]-4-(pyrimidin-2-yl)piperazine or a physiologically tolerable acid addition salt thereof.

4. A pharmaceutical composition containing as active ingredient a compound of claim 3 in an amount of 25 to 250 mg, together with a suitable pharmaceutical carrier.

5. A method for treating a living animal body afflicted with central nervous system disorders, comprising the step of administering an amount of a compound of claim 3 which is effective for the alleviation of the said conditions.

* * * * *